United States Patent [19]

Caldwell

[11] Patent Number: Plant 5,863

[45] Date of Patent: Jan. 20, 1987

[54] SPATHYPHYLLUM PLANT "JEANENE"

[76] Inventor: Edward B. Caldwell, 199 Townsend house Rd., Brooksville, Fla. 33512

[21] Appl. No.: 746,850

[22] Filed: Jun. 20, 1985

[51] Int. Cl.[4] ..... A01H 5/00

[52] U.S. Cl. ..... Plt./88

[58] Field of Search ..... Plt./88

*Primary Examiner*—James R. Feyrer

*Attorney, Agent, or Firm*—Frank B. Robb

[57] ABSTRACT

A variety of spathyphyllum plant having good wintertime greenish yellow overall appearance somewhat darker than prior spathyphyllum plants, the leaves being of thick elliptical shape with width about half that of the length, the plant having very good keeping qualities with resistance to cold weather, bruising and low nutrient levels without tip burn, attractive ovate blooms, and erect habit with stiff petioles.

1 Drawing Figure

GENERAL DESCRIPTION OF THE INVENTION

As a foliage plant grower, I have had a number of opportunities to observe various varieties of plants growing in my greenhouse in the area of Brooksville, Fla. and among a number of them which attracted my attention as a seedling was a spathyphyllum plant which was particularly noticeable because even as a relatively small plant eight inches high, it displayed dark green oval leaves and a compact growth which seemed to me to be desirable in a commercial plant. In addition its wintertime color which is a decided green was of interest and I therefore selected this specific seedling for further work and reproduction. I now identify the same as "Jeanene" which appears to be a cross of a noncommercial variety which I have had in my greenhouse and which is designated Maunaloa "Leslie".

I believe that the variety of my invention is a cross of the aforesaid plant and Floribunda×Tasson.

It is my opinion that the color of this plant is new to the small size of spathyphyllum and as such is attractive from the standpoint of the ultimate consumer.

The leaves of the plant in their green color are also thick, eliptical and have been found to be very resistant to cool weather chloroplast degradation.

I have caused this plant to be asexually reproduced by availing of lateral shoots and am currently further reproducing the same by tissue culture and testing the same in my nursery.

Further observations of this plant have convinced me that it has very good keeping qualities and as such is a desirable commercial ornamental. The fact that the leaves are thicker than usual enables them to resist bruising and thus the shipping damage is very much reduced.

The characteristic of this plant as far as the leaves are concerned is that they are eliptical and it is noted that the blooms which are shown in the drawing are substantially ovate, the leaves having very deep undulations on mature leaves. This is a further distinction which sets the plant apart from other varieties of spathyphyllum.

The relative size of the leaves is such that they are about fifty-five percent as wide as they are long and this seems to be a characteristic which is continuing to be noted in reproduced plants.

The plant form itself appears to be erect and open with stiff petioles.

Further important improvements which this variety of spathyphyllum seems to carry, are the ability to remain green even during cold weather and withstand excessive and inadequate nutrient levels without tip burn or paleness. The ability to tolerate low light levels is a valuable attribute likewise.

Attached to this application and a part thereof, is the drawing which illustrates a plant of my new variety and it is disclosed in color which is as nearly representative of the color which is a primary characteristic as is possible to make the same in an illustration of this kind and to reproduce it for study. It should be noted and attention is called to the fact that the light reflection on the leaves also causes a variation in color from that which might be observed under other circumstances. This reproduction is however very representative and provides the overall appearance which a plant of my new variety displays generally.

There follows a detailed description of my new variety with color terminology in accordance with the Munsell Color Chart published by Munsell Color Company, Inc. and known as the Nickerson Color Fan, except where general color terms of ordinary significance may be applicable and are made by me personally, therefore being subject to my own judgment and evaluation as to color comparisons which I nevertheless believe to be accurate and when compared with the color chart clearly descriptive of my variety.

FORM CHARACTERISTICS

1. Leaf shape:
   a. *Mature.*—Elliptic.
   b. *Immature.*—Elliptic.
   c. *Tip.*—Acute.
   d. *Base.*—(1) Mature: Cordate. (2) Immature: Cordate.
   e. *Veination.*—Heavily sunken.
2. Leaf attachment: Stalked.
3. Leaf arrangement: Alternate; horizontal.
4. Petiole: Medium length; winged; erect.
5. Stem: Short; heavy internodes; about one inch spacing.
6. Overall appearance: Medium dense to open.

SIZE CHARACTERISTICS OF TYPICAL COMMERCIAL SIZE IN 14" POTS

1. Leaf itself:
   a. *Width-widest point.*—Nine inches.

b. *Width*-1" *from tip.*—2".
c. *Length.*—16".

2. Petiole:
a. *Length.*—13½".
b. *Diameter* (*center*).—⅜–½.
c. *Internode spacing.*—¾ to 1".
d. *Stem diameter.*—2".

3. Bloom:
a. *Length.*—9".
b. *Width.*—6".
c. *Color.*—White.

COLOR CHARACTERISTICS

1. Leaf:
a. *Top* (*new leaves*).—7.5GY 7/9.
b. *Bottom overlay.*—7.5GY 8/7.
c. *Margin.*—7.5GY 8/7.

2. Leaf (old bottom leaves):
a. *Top.*—5GY 3/2.
b. *Bottom.*—7GY 4/4.

c. *Margin.*—7GY 4/4.

3. Leaf veination (underside):
a. *Midrib.*—7.5 GY 7/9.
b. *Veins.*—7.5 GY 7/9.

4. Stem: 5GY 4/3.
5. Petiole: 5GY 4/3.
6. Bloom: White.

I claim:

1. A new and distinct variety of spathyphyllum plant, substantially as herein shown and described, characterized particularly as to novelty by the unique combination of overall good winter color with greenish yellow upper surface of new leaves to greenish yellow surface of more mature leaves, good keeping qualities, the thick elliptic leaves being resistant to bruising with deep undulations as well as to cool weather chloroplast degradation, the plant as a whole being erect, with stiff petioles.

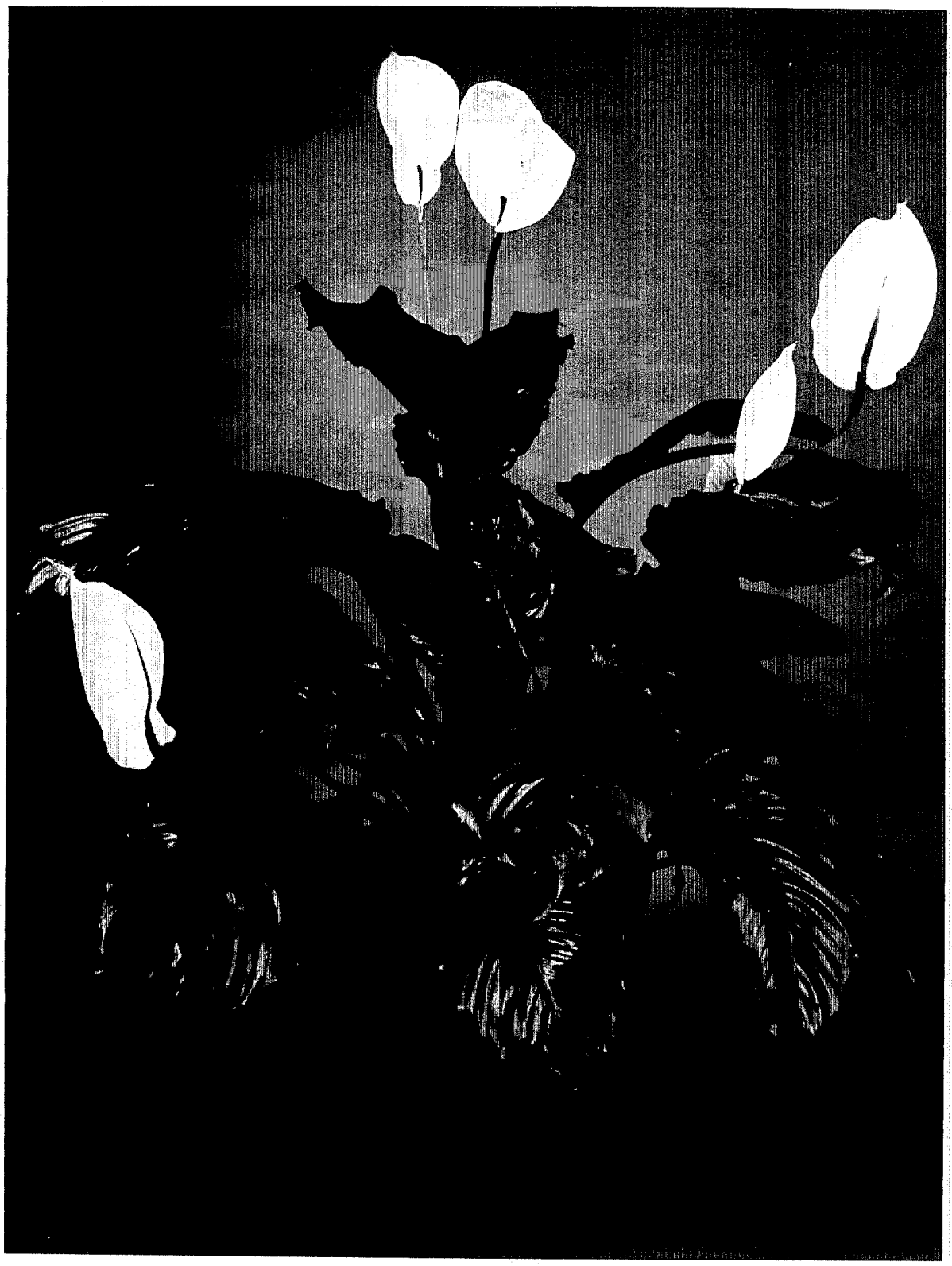

* * * * *